United States Patent
Fischer (10) Patent No.: US 6,234,795 B1
(45) Date of Patent: May 22, 2001

(54) FLEXIBLE MIXER EXTENDER

(75) Inventor: Dan E. Fischer, Sandy, UT (US)

(73) Assignee: Ultradent Products, Inc., Sandy, UT (US)

( * ) Notice: Subject to any disclaimer, the term of this patent is extended or adjusted under 35 U.S.C. 154(b) by 0 days.

(21) Appl. No.: 09/489,758

(22) Filed: Jan. 21, 2000

(51) Int. Cl.⁷ ....................................................... A61C 5/04
(52) U.S. Cl. ............................................. 433/90; 222/137
(58) Field of Search ........................ 433/89, 90; 222/137, 222/145.4, 145.5, 145.6, 527

(56) References Cited

U.S. PATENT DOCUMENTS

| | | | |
|---|---|---|---|
| 3,451,393 | * 6/1969 | Sarnoff | 222/145.4 |
| 4,067,479 | * 1/1978 | Moline | 222/137 |
| 4,674,658 | * 6/1987 | Van Brocklin | 222/137 |
| 4,958,750 | * 9/1990 | Palmert et al. | 222/145.4 |
| 4,979,942 | * 12/1990 | Wolf et al. | 222/137 |
| 5,029,738 | * 7/1991 | Dillon | 222/527 |
| 5,249,716 | * 10/1993 | O'Sullivan | 222/527 |
| 5,249,862 | * 10/1993 | Herold et al. | 222/137 |
| 5,413,253 | * 5/1995 | Simmen | 222/137 |
| 5,848,894 | * 12/1998 | Rogers | 433/90 |

FOREIGN PATENT DOCUMENTS

| | | | |
|---|---|---|---|
| 319639 | * 6/1989 | (EP) | 433/90 |
| 161955 | * 7/1988 | (JP) | 433/90 |

* cited by examiner

*Primary Examiner*—Todd E. Manahan
(74) *Attorney, Agent, or Firm*—Workman, Nydegger & Seeley (57) ABSTRACT

A dispensing system for dispensing first and second materials to a desired location within the mouth of a patient, includes: (i) a two-part material delivery system; (ii) a hollow delivery tip configured to deliver material to a specific location within a patient's mouth; and (iii) a hollow, flexible adaptor configured to flexible couple the delivery tip in fluid communication with the two-part material delivery system. The flexible adaptor enables the practitioner to move the delivery tip to a specific location within the patient's mouth without requiring that the delivery system be moved adjacent the mouth. Thus, the flexible adaptor enables a practitioner to deliver freshly mixed first and second materials to a specific desired location within the mouth of a patient.

19 Claims, 5 Drawing Sheets

FLEXIBLE MIXER EXTENDER

BACKGROUND OF THE INVENTION

1. The Field of the Invention

This invention is in the field of dispensing devices. More particularly, this invention relates to medical and dental dispensing devices for mixing and dispensing two-part materials to a desired location.

2. The Relevant Technology

Many modern formulations are packaged in two parts, often known as "A and B components" or "first and second materials". Upon mixing, these A and B components typically undergo a chemical reaction which causes the resultant composition to "set up" in some desired manner. In the dental field, for example, several two-part formulations currently enjoy wide use, such as cements and resinous materials. Dental impression materials are also typically made using A and B components.

In order to function properly, the A and B components should be mixed together rapidly and thoroughly and in the right proportions. Failure to mix rapidly can result in loss of valuable working time with the resultant composition, and can impact the ability to obtain a thorough mix as the composition begins to set up unevenly. Failure to mix thoroughly can result in a composition having less than optimum characteristics. For example, if a poorly mixed composition is used as a cement, it is possible that portions of the cement will fail to reach the chemical strength required for a long-term bond.

A typical method employed for mixing A and B components has been simple mechanical mixing through the use of a mixing bowl or pad, and a stir instrument such as a spatula. This method tends to be somewhat messy and time consuming. It is also difficult at times to gauge whether the mixing has been sufficiently thorough.

Further, many dental compositions are ultimately dispensed from a syringe in order to control the amount dispensed, to permit precise placement of the dental composition, and prevent premature evaporation of constituents of the composition. The use of a syringe is highly advantageous for the delivery of a dental composition in light of the ability to easily maneuver a syringe into tight places, such as between teeth and gums. Despite the many advantages of syringe delivery, syringe delivery typically requires the placement of a mixed composition into a syringe, which adds time to the procedure.

Although syringes are highly maneuverable even in tight places, the loss of working time associated with the loading of syringes has caused many practitioners to seek alternative methods for delivering a two-part material into the mouth of a patient For example, in an effort to overcome the time delay associated with placing a mixed two-part composition into a syringe, attempts have been made to mix materials delivered from a caulking gun-type extrusion device.

Typical caulking gun-type extrusion devices comprise a large and bulky device having a receiving area which receives one end of a dual barrel cartridge. Typical dual barrel cartridges have first and second materials therein which are held in separate barrels at a proximal end by movable plugs and which have a selectively closable opening at a distal end thereof. The receiving area also has first and second plungers coupled to a trigger.

Upon coupling the dual barrel cartridge into the receiving area, the plungers are aligned within respective barrels. The practitioner can then actuate the trigger, causing the plungers to advance within the barrels. This forces the first and second materials from respective barrels of the cartridge. A single mixing tube is typically coupled to the exit end of each of the barrels. The first and second materials are typically forced into the mixing tube where the materials are mixed. Typical mixing tubes have a mixing vane therein which is configured to mix the materials upon delivery through the mixing tube.

Figure 1:
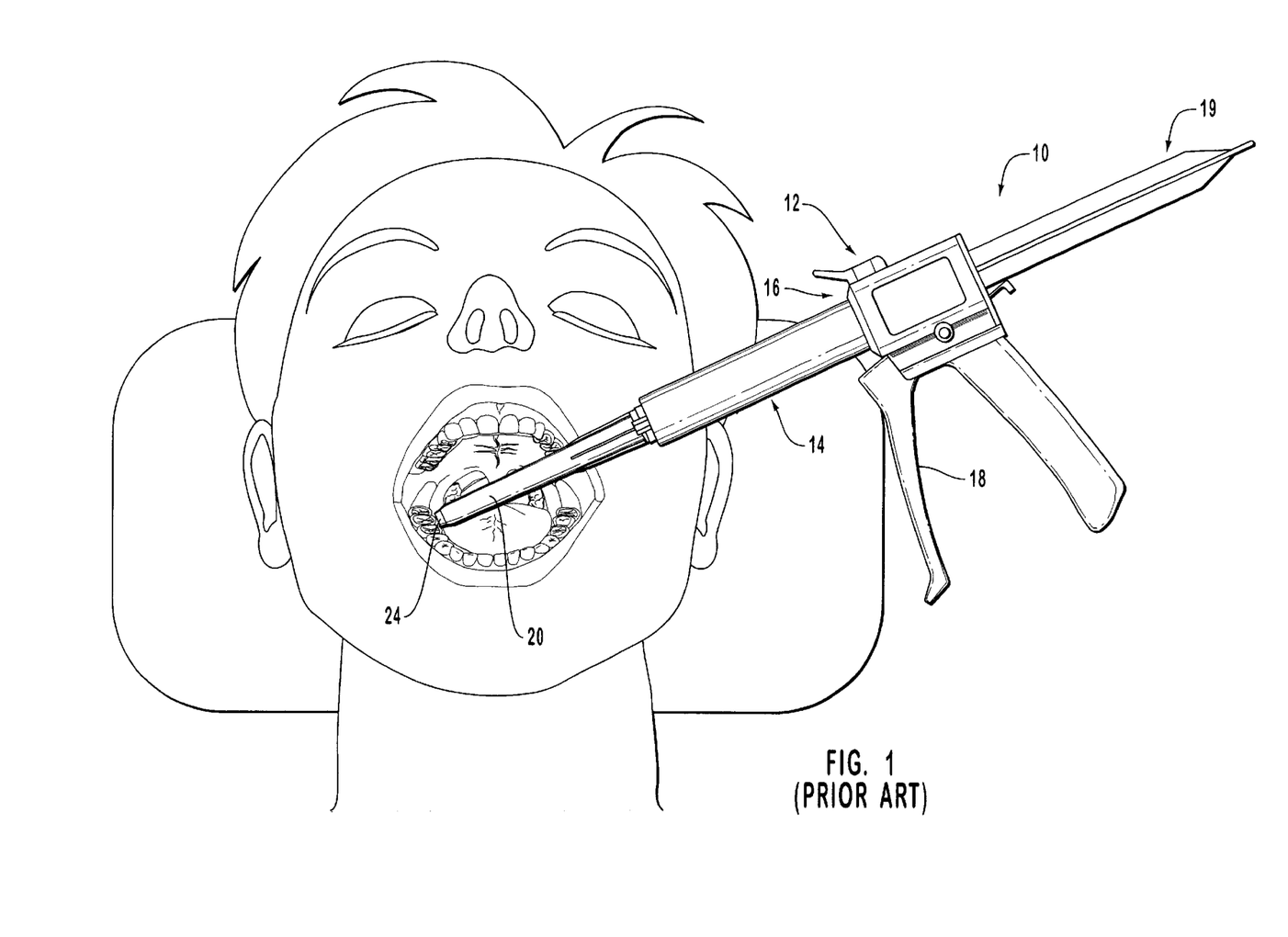
FIG. 1 is a view of a prior art dispensing system for dispensing a two-part material into the mouth of a patient.

FIG. 1 depicts a prior art version of such a two-part material dispensing system 10 featuring a caulking gun type extruder 12 having a dual barrel cartridge 14 selectively coupled thereto. The cartridge 14 is coupled to a receiving area 16 of the extrusion apparatus 12. Upon actuating a trigger 18 of the extruder 12, first and second plungers 19 (only one plunger 19 shown) of the extruder 12 advance into respective barrels of cartridge 14, forcing the first and second materials within the first and second barrels of cartridge 14 into a mixing tube 20 having a mixing vane (not shown) therein. The first and second materials expressed from the separate barrels of cartridge 14 are mixed as they proceed along mixing tube 20. The mixed material is then forced out of distal tip 24 of mixing tube 20 and into the mouth of the patient.

As depicted in FIG. 1, the use of the prior art caulking gun-type dispensing system 10 is awkward. The practitioner is required to hold the entire system 10, which is large and cumbersome, adjacent the mouth of the patient, then attempt to deliver first and second materials within cartridge 14 to a specific location within the mouth of the patient. The weight of the dispensing system 10 along with its length and overall bulkiness can combine to make this procedure quite difficult and frustrating both for (i) the practitioner, who is required to hold, aim and actuate the dispensing system 10; and (ii) the patient, who must endure the placement of such a large, bulky instrument adjacent his or her head.

To compound this frustration, the strain accompanying the compression of trigger 18 while holding the bulky system 10 adjacent the patient's mouth can cause the practitioner's hand to shake during delivery of the composition, further decreasing the accuracy of the delivery of the composition into a precisely desired location within the mouth of a patient.

There is therefore, a need in the art for a dispensing system which is readily maneuverable without allowing a two-part material to harden prematurely. There is also a need in the art for a dispensing system which is not bulky and can be readily actuated by a practitioner. There is also a need in the art for a maneuverable dispensing system which can be used to dispense material directly and conveniently into small spaces within the patient's mouth, such as between the patient's teeth and gums without employing a prematurely hardened material.

SUMMARY AND OBJECTS OF THE INVENTION

It is therefore an object of the invention to provide an improved two-part material dispensing system.

It is another object of the invention to provide a two-part material dispensing system which is convenient for a practitioner to maneuver and which supplies a freshly mixed composition to a specific desired site within the mouth of a patient.

It is another object of the invention to provide a dispensing system which enables a practitioner to conveniently deliver a mixed two-part composition to a specific desired location within a patient's mouth, such as between a patient's teeth and gums.

A dispensing system of the present invention comprises a flexible hollow adapter which flexibly couples a two-part material delivery system (i.e., a system which delivers first and second materials, also known as "A" and "B" components) to a hollow delivery tip.

The flexible adapter comprises: (i) a flexible, elongate tube having a proximal end and a distal end; (ii) a proximal coupling collar coupled to the proximal end of the elongate tube; and (iii) a distal coupling collar coupled to the distal end of the elongate tube. The proximal coupling collar is configured to be selectively, removably coupled to the two-part material delivery system. The distal coupling collar is configured to be selectively, removably coupled to the hollow delivery tip.

Material from the two-part material delivery system (such as an extruder having a dual barrel cartridge coupled thereto) flows through the flexible, hollow adaptor to the delivery tip. The delivery tip may comprise a mixing tube having one or more mixing vanes therein, for example. In one embodiment, a curved end portion is coupled to the mixing tube portion, forming a convenient, maneuverable, mixing delivery tip.

By using the flexible adaptor, the practitioner is able to dispense a freshly mixed two-part composition through a conveniently maneuverable delivery tip, such as a substantially rigid, hollow delivery tip. The delivery tip coupled to the adaptor can be maneuvered into a variety of a different, fine-tuned locations after which the material delivery system can be actuated. Material is delivered through the adaptor and tip to the desired location. Thus, a practitioner is able to readily deliver material through the delivery tip between the teeth and gums of a patient or to another specific location within the mouth of a patient.

Also, in light of the flexible adapter, a practitioner has a variety of different options for delivering a freshly mixed two-part material. For example, the practitioner can (i) use one hand to hold the delivery tip strategically within a patient's mouth; and (ii) simultaneously hold and actuate a material delivery system (e.g., a caulking gun-type extruder with a dual barrel cartridge thereon or other two-part material delivery system) with an opposing hand.

According to another technique, however, a dental practitioner holds the delivery tip adjacent the desired location within the patient's mouth while an assistant holds the two-part material delivery system. The practioner then signals the assistant to begin actuating the two-part material delivery system until a desired amount of mixed two-part material is delivered. The two-part material delivery system can be the manually activated type shown in detail in the drawings or alternatively the two-part material delivery system can be automated so that it is unnecessary to exert significant force to delivery the materials to the flexible adapter and the tip. Thus, a practitioner has a variety of different options which are afforded through the use of a flexible adapter which couples a delivery tip to the two-part material delivery system.

Consequently, a dispensing system employing the invented flexible adapter tube features; (i) the advantages of a small, maneuverable delivery tip; and (ii) the advantages of a typical caulking gun-type extruder which delivers a fresh two-part material. The flexible adaptor tube also eliminates the shaking problems associated with the compression, holding, and aiming of heavy, bulky dispensing systems of the prior art. Rather than being required to hold and actuate an entire dispensing system adjacent the patient's mouth, a practitioner is only required to hold and aim the delivery tip within a patient's mouth.

The flexible adapter of the present invention may take a variety of different forms. In a first embodiment, the flexible adapter tube comprises a hollow tubular member. A two-part material flows from the two-part material delivery system through the adaptor into the delivery tip. As indicated above, the delivery tip may, for example, comprise a substantially rigid mixing tube having one or more mixing vanes therein.

In another embodiment, the flexible adapter comprises a flexible tube having a septum therein, creating first and second longitudinal passageways. The septum can be configured to be aligned with a septum of a dual barrel cartridge of the delivery system, for example, thereby retaining the two-part material in a separated state until the two-part material reaches a mixing tube coupled to the adaptor.

In yet another embodiment, the flexible, elongate adaptor tube itself has one or more mixing vanes therein such that the material is mixed within the tube while being delivered from the proximal end of the tube to a distal end of the tube. In this embodiment, it is possible for a practitioner to deliver freshly mixed material directly from the adaptor tube.

In order to retain the material disposed within the tube in a fresh state between uses, a cover is provided which selectively, removably couples about the flexible tube.

These and other objects and features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to a specific embodiment thereof which is illustrated in the appended drawings. Understanding that these drawings depict only a typical embodiment of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

Figure 2:
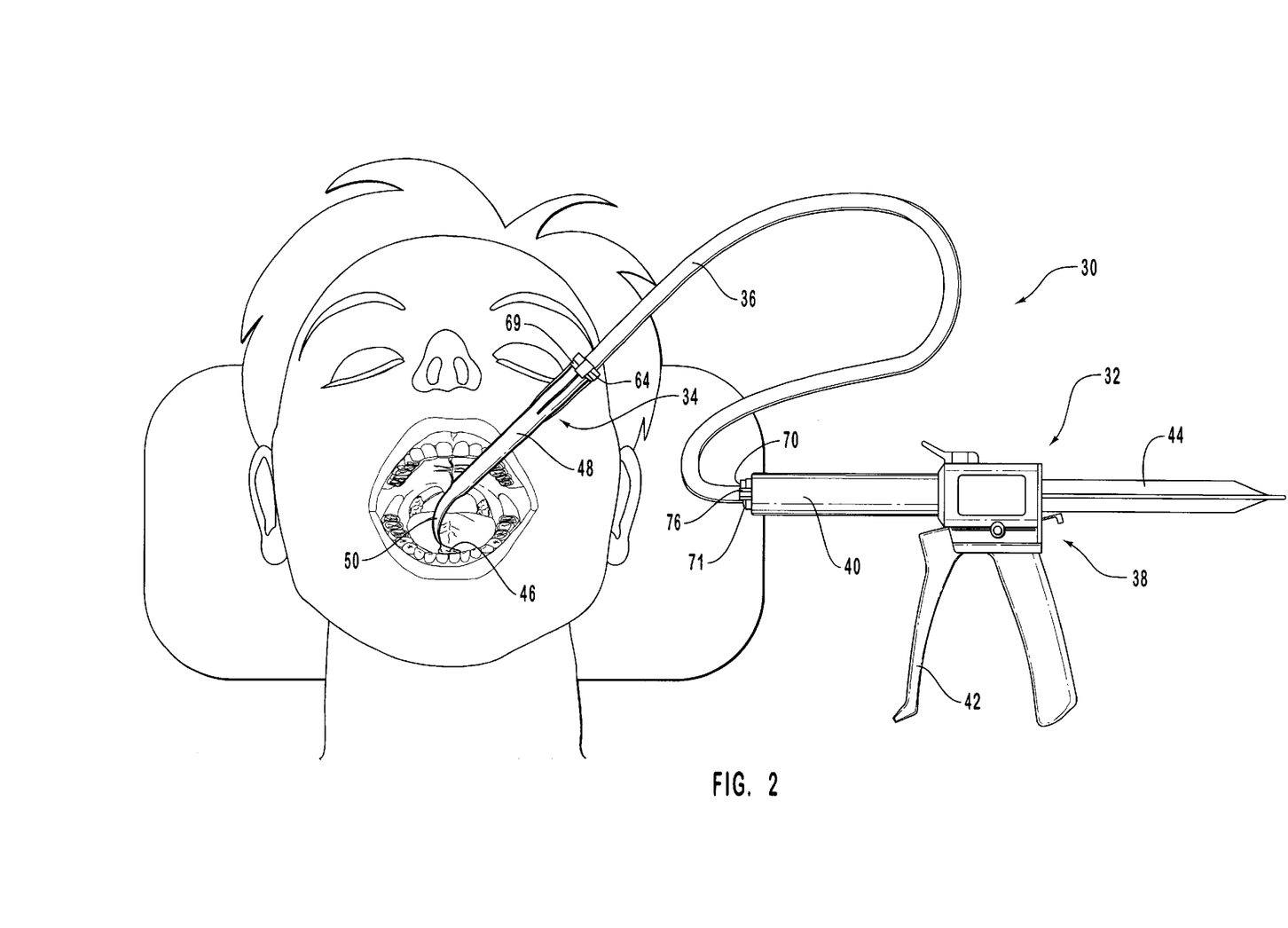
FIG. 2 is a perspective view of a two-part material dispensing system of the present invention, employing an adaptor and delivery tip of the present invention.

With reference now to FIG. 2, a dispensing system 30 for mixing and delivering a two-part material is shown. Dispensing system 30 comprises (i) a two-part material delivery system 32; (ii) a delivery tip 34; and (iii) a flexible, hollow adaptor 36 flexibly coupling material delivery system 32 in fluid communication with delivery tip 34.

As depicted in FIG. 2, in light of the use of flexible adaptor 36, delivery tip 34 may be maneuvered, aligned, and aimed within the mouth of a patient remotely from material delivery system 32. Furthermore, a practitioner holding tip 34 is not required to simultaneously hold two part material delivery system 32 in the same hand. Instead, the practitioner can hold tip 34 in one hand and actuate material delivery system 32 with another hand. Optionally, one practitioner can hold delivery system 32 while another practitioner focuses on orienting and holding tip 34 in a precise location within a patient's mouth.

Delivery system 32 is an example of a means for delivering first and second materials to a desired location. System 32 comprises a caulking gun-type extruder 38 having a dual-barrel cartridge 40 selectively, removably coupled thereto. Adaptor 36 is selectively, removably, coupled to dual barrel cartridge 40 of material delivery system 32 and to tip 34.

Upon actuating a trigger 42 of extruder 38, first and second plungers 44 (only one plunger 44 shown) of extruder 38 advance into respective barrels within cartridge 40, forcing the different materials within cartridge 40 into adaptor 36. Continual actuation of trigger 42 causes the material advanced into adaptor 36 to advance into delivery tip 34, wherein the materials are thoroughly mixed. The mixed material 46 can then be deposited into the mouth of the patient, as shown in FIG. 2.

Delivery tip 34 may be comprised of a variety of different components. Tip 34 is preferably substantially rigid. Delivery tip 34 preferably comprises a proximal mixing portion 48 and a distal delivery end portion 50 coupled thereto which is preferably a curved end portion as shown at 50 in FIG. 2. In a preferred embodiment, proximal mixing portion 48 of delivery tip 34 is a substantially rigid tubular member having one or more mixing vanes therein. Proximal mixing portion 48 is thus an example of a mixing tube.

Another example of a delivery tip and/or a dual barrel cartridge which may be employed in the present invention by being coupled to adaptor 36 is disclosed in U.S. Pat. No. 4,767,026 to Keller, which is incorporated herein by reference. Other delivery tips and dual barrel cartridges may also be employed, such as those known in the art.

Flexible adaptor 36 is configured for flexibly coupling a two-part material delivery system such as system 32 and to a hollow delivery tip such as tip 34. The first and second materials within the separate barrels of cartridge 40 are mixed somewhat as they proceed along hollow adaptor 36. The materials are more thoroughly mixed in mixing tube 48 of delivery tip 34. The mixed material 46 is then forced out of delivery tip 34 and into the mouth of the patient during continued actuation of trigger 42.

In another embodiment, material is mixed more thoroughly in the adaptor, as discussed below with respect to FIG. 8. In yet another embodiment, the materials are kept separate until reaching the mixing tube, as described below with respect to FIG. 7. In the embodiment of FIG. 2, delivery tip 34 is selectively, removably coupled to adaptor 36.

Figure 3:
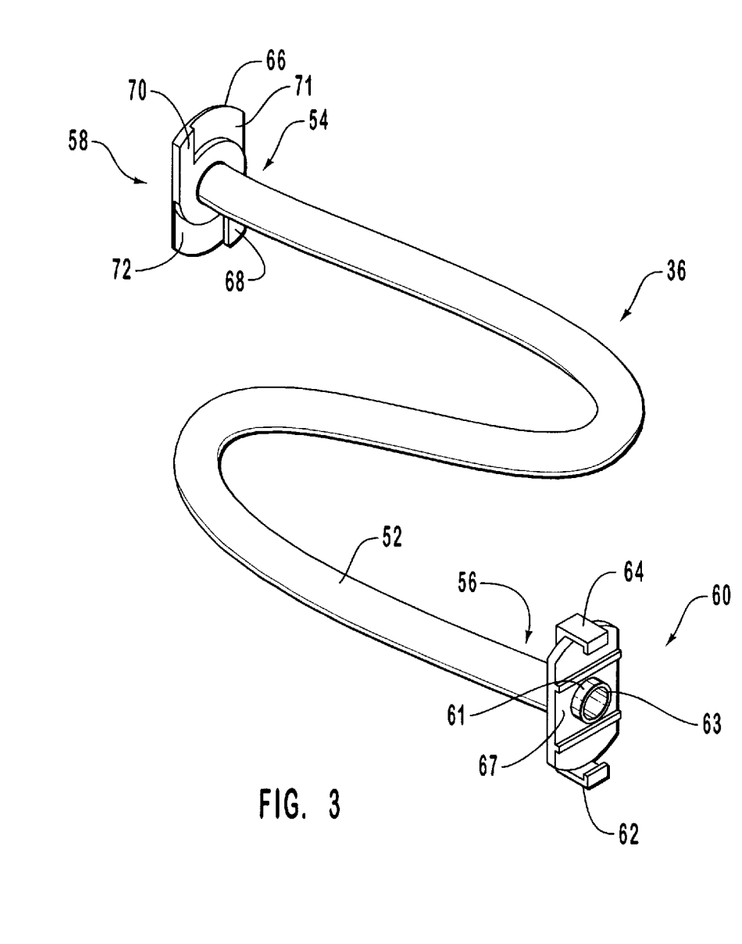
FIG. 3 is a perspective view of the adaptor of FIG. 2.
Figure 4:
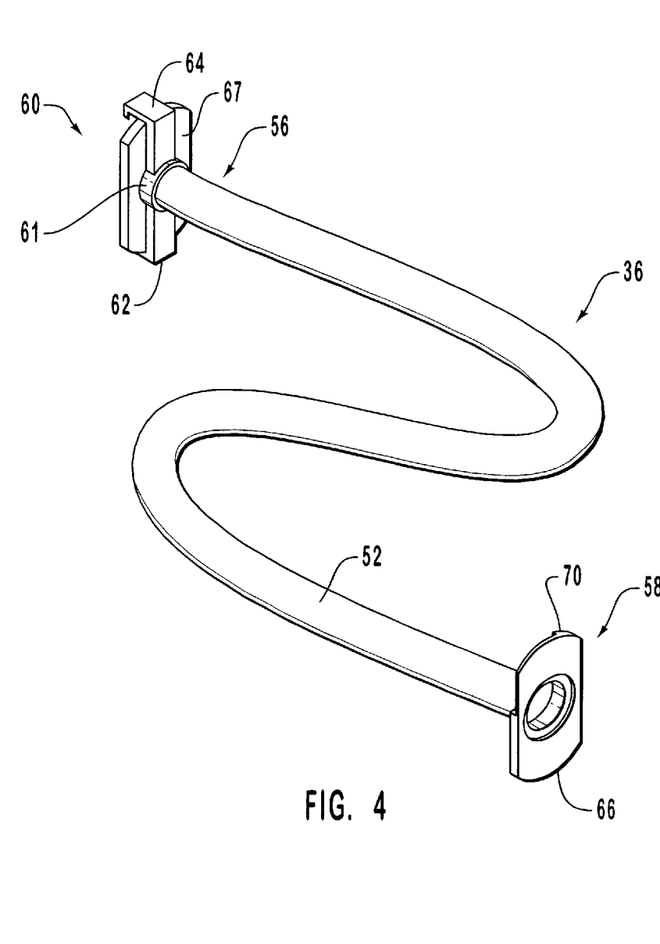
FIG. 4 is an opposing perspective view of the adaptor of FIG. 2.

With reference now to FIGS. 3 and 4, which show opposing perspective views of adaptor 36, flexible adaptor 36 will now be discussed in additional detail. Flexible adaptor 36 comprises: (i) a flexible elongate tube 52 having a proximal end 54 and a distal end 56; (ii) proximal coupling collar 58 coupled to proximal end 54 of flexible elongate tube 52; and (iii) a distal coupling collar 60 coupled to distal end 56 of flexible elongate tube 52. Proximal coupling collar 58 is configured to be coupled to a two-part material delivery system. Distal coupling collar 60 is configured to be coupled to a hollow delivery tip.

Flexible elongate tube 52 may be comprised of a variety of different materials, such as polyethylene, polycarbonate, neoprene, and polypropylene, by way of example. However, a variety of different flexible materials may be employed which are capable of being made in a flexible, tubular, elongate form. Proximal and distal coupling collars 58, 60 may also be comprised of materials such as polyethylene, polycarbonate, neoprene, and polypropylene, by way of example, or a variety of different materials. Coupling collars 58 and 60 may be substantially rigid, but are optimally flexible and pliable. Collars 58, 60 can be formed separately from or integrally with tube 52.

Coupling collars 58, 60 selectively, removably couple in mating relationship with system 32 and delivery tip 34, respectively, such that adaptor system 32, tip 34, and adaptor 36 are in fluid communication. The proximal and distal coupling collars of an adaptor of the present invention may selectively, removably interlock with a two-part material delivery system and a delivery tip, respectively, in a variety of different manners, such as through mating threads, a press fit, or other interlocking relationships known in the art or yet to be produced. In the embodiments of FIGS. 3–4, coupling collars 58, 60 selectively, removably interlock with system 32 and tip 34, respectively, through the use of claws and flanges which interlock upon being twisted with respect to each other.

For example, with continued reference to FIGS. 3–4, proximal coupling collar 58 is configured to selectively, removably couple in interlocking, mating relationship with two-part material delivery system 32. Proximal coupling collar 58 comprises an oblong shaped hollow flange 66 having stops 68, 70 and wings 71, 72, which are preferably at least partially tapered.

Distal coupling collar 60 is configured to selectively, removably couple in interlocking, mating relationship with delivery tip 34. Distal coupling collar 60 comprises a hollow neck 61 coupled to tube 52. A distal portion 63 of neck 61 selectively, removably mates within delivery tip 34 such that tip 34 and tube 52 are in fluid communication. First and second claws 62, 64 extend from neck 61. Coupling collar 60 further comprises a plate 67 which is coupled to neck 61.

Figure 5:
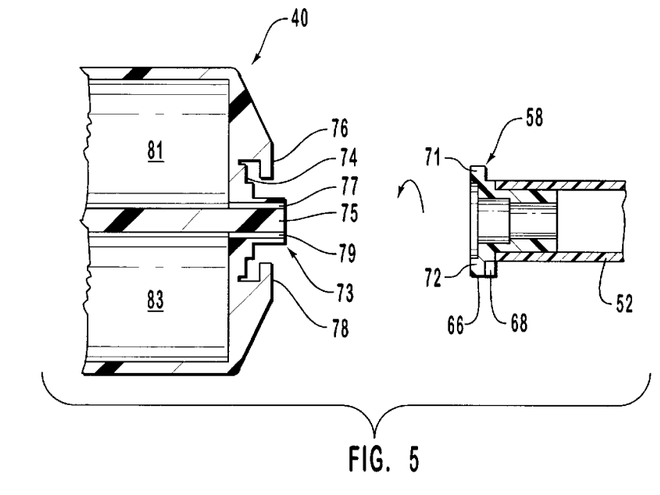
FIG. 5 is a cutaway cross-sectional view of a two-barrel cartridge exploded from a cutaway cross-sectional view of a proximal end of the adaptor of FIG. 2.
Figure 6:
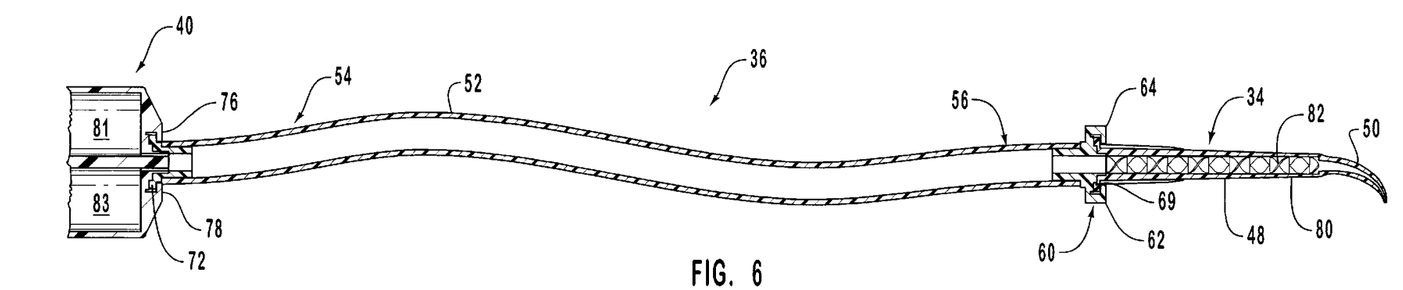
FIG. 6 is a cut-away side view of the dispensing system of FIGS. 2–5, comprising an adaptor selectively, removably coupled between a two-part material delivery system and a delivery tip.

With reference now to FIGS. 5 and 6, in the embodiment shown, dual barrel cartridge 40 has a distal neck 73. Neck 73 has first and second distal openings 77, 79 of first and second barrels 81, 83, respectively, therein. Openings 77, 79 are separated by a septum 75 in neck 73. Neck 73 selectively, removably mates within proximal coupling collar 58. The selective, interlocking coupling of proximal coupling collar 58 to dual barrel cartridge 40 will now be discussed in further detail with continued reference to FIGS. 5 and 6.

During the coupling procedure, oblong flange 66 is initially moved past claws 76, 78 of cartridge 40 such that flange 66 abuts distal plate 74 of cartridge 40. This may be accomplished, for example, by twisting flange 66 a quarter turn with respect to the orientation of flange 66 in FIG. 5 (as shown by the arrow in FIG. 5) such that flange 66 can be moved past claws 76, 78. Upon moving flange 66 past claws 76, 78, neck 73 of cartridge 40 is disposed through hollow flange 66 in mating relationship with coupling collar 58. Thus, barrels 81, 83 of cartridge 40 and adaptor tube 52 are in fluid communication To selectively, removably interlock flange 66 with cartridge 40, flange 66 is twisted a quarter turn such that wings 71, 72 of flange 66 are detachably mounted between distal plate 74 and respective first and second claws 76, 78 of cartridge 40, as shown in FIG. 6. Stops 68, 70 (FIGS. 3–5) abut against respective claws 78, 76 after flange 66 is twisted a quarter turn, as also depicted in FIG. 2.

Proximal coupling collar 58 is an example of means for coupling tube 52 to a two-part material delivery system. However, the proximal coupling collar may be configured in a variety of different manners, such as by having first and second claws which grip a flange, threads which mate with mating threads on the two-part material delivery system, a press fitting member, or a variety of other examples of means for coupling tube 52 to a two-part material delivery system. In yet another embodiment, the means for coupling the elongate flexible tube of an adaptor of the present invention to a two-part material delivery system comprises the proximal end of the elongate tube being configured to be coupled directly to the two-part material delivery system.

With continued reference to FIG. 6, claws 62, 64 of distal coupling collar 60 selectively, interlockingly, couple to a delivery tip in the manner of a quarter turn fastener similar to the quarter turn fastening described above with respect to proximal coupling collar 58. For example, as shown in FIG. 6, claws 62,64 couple to an oblong shaped flange 69 of delivery tip 34 in interlocking relationship as flange 69 is twisted between claws 62, 64 and plate 67 of distal coupling collar 60. The coupling of claws 64 to plate 69 is also depicted in FIG. 2. Tapered wings and stops which stop against respective claws 62,64 may also be employed on flange 69 of delivery tip 34, as discussed with respect to proximal coupling collar 58. Although a variety of designs may be employed, in one embodiment, flange 69 of delivery tip 34 is similar or identical to flange 66 of coupling collar 58.

Distal coupling collar 60 is an example of means for coupling tube 52 to a delivery tip. However, the distal tip may have a variety of different configurations, such as a flange which is grasped by first and second claws, threads which mate with mating threads on the delivery tip, a press fit, or a variety of other examples of means for coupling tube 52 to a delivery tip. In yet another embodiment, the means for coupling the elongate flexible tube of an adaptor of the present invention to a delivery tip comprises the distal end of the elongate tube being configured to be coupled directly to the delivery tip.

With continued reference to FIGS. 5 and 6, proximal and distal coupling collars 58, 60 are coupled to proximal and distal ends 54, 56, of tube 52, respectively, such as by being fused thereto or secured thereto through the use of an adhesive, heat bonding, tight fit, or a variety of other manners known or yet to be introduced into the art. In another embodiment of the invention, however, the proximal and/or distal collars are coupled to the tube by being an integral extension of the tube. Also as shown, flexible elongate tube 52 is a hollow tube without a septum or a mixing vane or other device or member therein.

Also as shown in FIG. 6, delivery tip 34 comprises (i) proximal mixing portion 48 featuring a hollow tube 80 housing one or more longitudinal extending mixing vanes 82; and (ii) curved hollow delivery end portion 50 coupled in fluid communication with proximal mixing portion 48. FIG. 6 demonstrates that one major advantage of flexible adaptor 36 and delivery tip 34 is that the practitioner can conveniently, precisely position a curved tip into a desired location within a patient's mouth. The ability to use a curved tip is a major advantage because it allows the practitioner to conveniently deliver material to a precisely desired location.

In one embodiment, mixing vanes 82 are similar or identical to the mixing vanes described in U.S. Pat. No. 4,767,026, which is incorporated by reference herein. However, the mixing vanes may be comprised of a variety of different mixing vane embodiments as will be appreciated by one skilled in the art in light of this disclosure.

Figure 7:
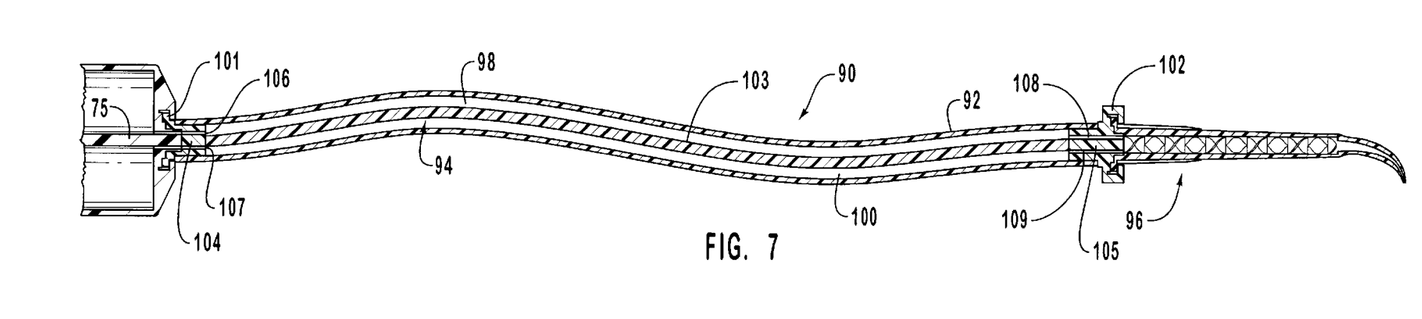
FIG. 7 is a view of an alternate adaptor of the present invention having a septum disposed along the length thereof.

With reference now to FIG. 7, another flexible, hollow adaptor 90 is shown. Adaptor 90 has a septum 94 extending therethrough along the length thereof. Septum 94 divides adaptor 90 into separate first and second lumens 98, 100. Adaptor 90 comprises a hollow elongate flexible tube 92. Adaptor 90 has a delivery tip 96 selectively, removably coupled thereto. Upon coupling to a two-part material delivery system, a septum (e.g., septum 75 of cartridge 40) of the two-part material delivery system can be placed in alignment with the septum 94 of adaptor 90 such that first and second lumens 98, 100 of adaptor 90 are in fluid communication with respective first and second barrels of the two-part material delivery system.

In the embodiment of FIG. 7, proximal and distal coupling collars 101, 102 are coupled to respective opposing ends of adaptor tube 92. Septum 94 comprises (i) a tube septum 103 extending along tube 92; and (ii) collar septums 104, 105 of respective collars 101, 102. Thus, first and second lumens 98, 100 extending along the length of adaptor 90 include respective first and second collar lumens 106, 107 extending through collar 101 and respective first and second collar lumens 108, 109 extending through collar 102. Consequently, first and second materials flowing through adaptor 90 remain separate until reaching tip 96, in which the materials are mixed.

Thus, the first and second materials expressed from the two-part material delivery system into adaptor 90 are retained in separate lumens 98, 100 until being mixed in delivery tip 96, which has one or more mixing vanes therein for mixing the materials. This separation preserves the first and second materials expressed into the different lumens 98, 100 of adaptor 90, but not expressed into delivery tip 96, for another use, thereby avoiding the mixing of materials which are not expressed from adaptor 90 into tip 96.

In the embodiment of FIG. 7, septums 103, 104, and 105 are separate septums which combine to form a single septum 94 extending along the length of adaptor 90. By way of example, the septums can be coupled together such as by being fused or secured through the use of an adhesive, heat bonding, or a variety of other manners known or yet to be introduced into the art. In another embodiment, septums 104, 105 and septum 103 are initially formed as a single, integral septum extending along the length of adaptor 90.

In these embodiments, septum 94 divides adaptor 90 into first and second separate lumens 98, 100 extending along the length of adaptor 90, such that first and second materials delivered from the two-part material delivery system are retained in the separate lumens 98, 100 until reaching hollow delivery tip 96, thereby preventing the first and second materials from mixing with each other until reaching delivery tip 96.

In another embodiment, septum 75 of the two-barrel cartridge is configured to be in a mating relationship with septum 94 of adaptor 90, to ensure proper alignment between septum 75 and septum 94. As one example of such a mating relationship, septum 94 can have a ridge (not shown) extending therefrom which mates within a groove (not shown) in septum 75. Optionally, septum 75 has a ridge which mates with a groove in septum 94.

Figure 8:
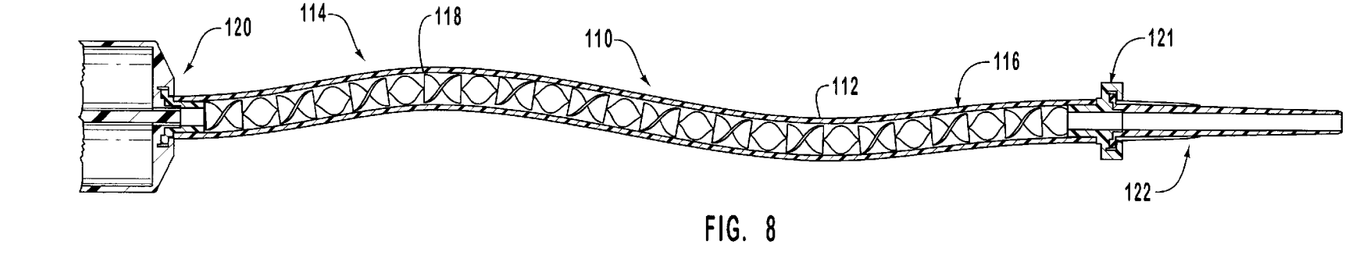
FIG. 8 is a view of an alternate adaptor of the present invention comprising an adaptor having a longitudinally extending mixing vane therein.

With reference now to FIG. 8, yet another embodiment of a flexible adaptor 110 of the present invention is shown. Flexible adaptor 110 comprises a hollow elongate flexible tube 112 having a proximal end 114 and a distal end 116 and at least one, and optionally a plurality, of mixing vanes 118 which are disposed longitudinally within hollow elongate flexible tube 112. Mixing vane(s) 118 can be moved in a variety of different directions consistent with the overall flexibility desired within adaptor 110.

In the embodiment shown, flexible adaptor 110 comprises a proximal coupling collar 120 coupled to proximal end 114 of tube 112 and a distal coupling collar 121 coupled to distal end 116 of tube 112. Proximal coupling collar 120 is configured to selectively, removably couple flexible adaptor 110 to a material delivery system while distal coupling collar 121 is configured to selectively, removably couple flexible adaptor 110 to a delivery tip 122 which may be configured with or without mixing vanes.

Optionally, it is possible to deliver freshly mixed material directly from distal end 116. Since adaptor 110 has its own mixing vane, adaptor 110 may be employed to deliver freshly mixed material and is flexible enough to be maneuvered to a desired location.

Figure 9:
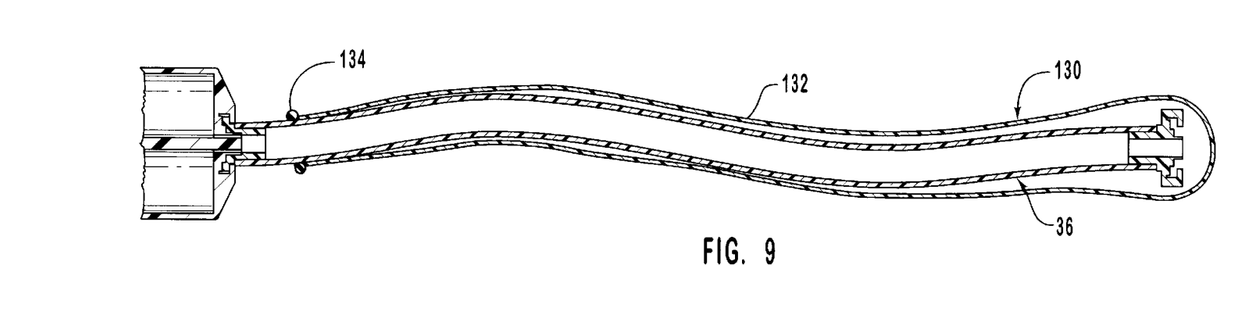
FIG. 9 is a view of an adaptor of the present invention having a cover selectively, removably placed thereon.

It is possible to selectively use and reuse an adaptor of the present invention such as flexible adaptor 36. To keep the adaptor 36 protected and clean between uses, a cover 130 (FIG. 9) may be selectively, removably coupled about the adaptor 36. Cover 130 can also conserve and protect material expressed into an adaptor after a first use, such that material retained in the adaptor can be used during subsequent uses (particularly when an adaptor such as adaptor 90 has a septum therein and retains the first and second materials in an unmixed state before reaching the delivery tip). In the embodiment of FIG. 9, cover 130 comprises a body portion 132 and a constriction portion 134 coupled to the body portion 132, the constriction portion 136 configured to grasp a portion of adaptor 36. In another embodiment, a cap is configured to be selectively, removably placed within distal collar 60 to thereby close adaptor 90.

As will be appreciated from the foregoing discussion, a variety of different means for delivering first and second materials to a desired location may be employed in the present invention, such as system 32. System 32 comprises (i) means for storing first and second materials; and (ii) means for selectively expressing first and second materials from the means for storing the first and second materials. Preferably, the means for storing the first and second materials is selectively, removably coupled to the means for selectively expressing the materials.

For example, dual barrel cartridge 40, which can be selectively, removably coupled to extruder 38, is an example of means for storing first and second materials. However, a variety of other examples of such storage means may be employed in the present invention, including, for example, separate barrels, a dual syringe apparatus, another dual tube apparatus, or a variety of different storage means which store first and second materials until the materials are expressed therefrom.

Caulking gun type extruder 38 is one example of a means for selectively expressing first and second materials from the means for storing the first and second materials. Other examples of means for selectively expressing first and second materials from the storage means include a motorized extruder, such as an electrical motorized extruder, a screw-driven extruder (such as a hand operated or motorized screw-driven extruder), a compression driver (such as an apparatus which blows air or another gas against the proximal ends of a dual barrel cartridge or which presses pistons into the different barrels of the cartridge), a single screw for each barrel of a cartridge or dual screws connected together (one for each barrel), or a variety of other devices which may be employed to express material from a dual barrel cartridge or other system for storing a two-part material until desired for use.

Another embodiment of means for delivering first and second materials to a desired location comprises a means for storing first and second materials which is nonremovably coupled to a means for selectively expressing first and second materials from the means for storing the first and second materials.

Flexible adaptors 36, 90, 110 are examples of means for flexibly coupling a delivery tip in fluid communication with means for delivering first and second materials to a desired location such that the material delivery system and the delivery tip are in fluid communication.

As discussed above, the dispensing system 30 of the present invention has a variety of different advantages, including the ability to aim and deliver a material to a precise location within a patient's mouth without sacrificing the ability to deliver fresh, newly mixed material. Other advantages include: (i) that material is not wasted by a practitioner who is unable to properly aim the delivery of the material; and (ii) that the operation of the device may be performed by a first and second persons or by single person using one hand to actuate the dispensing system 30 and a second hand to aim the delivery tip.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by united states Letters Patent is:

1. A dispensing system for dispensing first and second materials to a desired location within the mouth of a patient, the dispensing system comprising:

means for separately delivering first and second materials;

a hollow delivery tip configured to direct material received within the tip to a specific desired location within a patient's mouth; and means for flexibly coupling the delivery tip in fluid communication with the delivering means such that the first and second materials are selectively delivered through the coupling means from the delivering means to the delivery tip while the delivering means is remotely held relative to the hollow delivery tip, wherein the coupling means has means for dividing the coupling means into first and second separate lumens along its length such that the first and second materials delivered from the delivering means are retained in the separate lumens until reaching the hollow delivery tip, thereby preventing the first and second materials from mixing with each other until reaching the delivery tip.

2. A dispensing system as recited in claim 1, wherein the means for delivering first and second materials to a desired location comprises:

means for storing first and second materials; and means for selectively expressing first and second materials from the means for storing the first and second materials.

3. A dispensing system as recited in claim 2, wherein the means for storing first and second materials comprises a dual barrel cartridge.

4. A dispensing system as recited in claim 3, wherein the means for selectively expressing first and second materials comprises an extruder, the cartridge being selectively, removably coupled to the extruder.

5. A dispensing system as recited in claim 1, wherein the hollow delivery tip comprises:

a proximal mixing tube portion; and a distal curved end portion coupled to the mixing tube portion.

6. A dispensing system as recited in claim 5, wherein the proximal mixing tube portion has at least one mixing vane therein.

7. A dispensing system as recited in claim 1, wherein the delivery tip is substantially rigid.

8. A dispensing system as recited in claim 1, wherein the means for flexibly coupling the delivery tip comprises a flexible, tubular adaptor.

9. A dispensing system as recited in claim 8, wherein the delivery tip is selectively, removably coupled to the adaptor.

10. A dispensing system as recited in claim 8, wherein the adaptor is configured to be selectively, removably coupled to the means for delivering first and second materials to a desired location.

11. A dispensing system as recited in claim 8, wherein the adaptor comprises:

a flexible, elongate tube having a proximal end and a distal end;

means for coupling the elongate tube to the means for delivering first and second materials to a desired location; and means for coupling the elongate tube to the delivery tip.

12. A dispensing system as recited in claim 11, wherein:

the means for coupling the elongate tube to the means for delivering first and second materials to a desired location comprises a proximal coupling collar coupled to the proximal end of the elongate tube, the proximal coupling collar configured to be coupled to the means for delivering first and second materials to a desired location, and wherein:

the means for coupling the elongate tube to a delivery tip comprises a distal coupling collar coupled to the distal end of the elongate tube, the distal coupling collar configured to be coupled to the delivery tip.

13. A flexible adaptor as recited in claim 11, wherein the means for coupling the elongate tube to the means for delivering first and second materials to a desired location comprises a proximal coupling collar which is configured to selectively, removably interlock in mating relationship with a distal delivery end of a dual barrel cartridge.

14. A dispensing system as recited in claim 8, wherein the adaptor comprises a flexible tube, wherein the dividing means is at least one septum in the adaptor, the septum defining first and second lumens extending along the length of the tube.

15. A dispensing system as recited in claim 1, wherein the first lumen is configured to be in fluid communication with a first barrel of the means for delivering first and second materials and the second lumen is configured to be in fluid communication with a second barrel of the means for delivering first and second materials.

16. A dispensing system for dispensing first and second materials to a desired location within the mouth of a patient, the dispensing system comprising:

a two-part material delivery system adapted to separately hold and deliver first and second materials;

a hollow delivery tip adapted to direct material received within the tip to a specific desired location within a patient's mouth; and a hollow, flexible adaptor which flexibly couples the delivery tip in fluid communication with the two-pat material delivery system such that the two-part material deliver system can be remotely held while delivering the first and second materials to the hollow delivery tip via the adaptor as the hollow delivery tip is positioned at a patient's mouth, wherein the adaptor has a septum therein, the septum dividing the adaptor into first and second separate lumens extending along the length of the adaptor, such that first and second materials delivered from the two-part material delivery system are retained in the separate lumens until reaching the hollow delivery tip, thereby preventing the first and second materials from mixing with each other until reaching the delivery tip.

17. A dispensing system for dispensing first and second materials, the dispensing system comprising:

a two-part material delivery system adapted to separately hold and deliver first and second materials;

a hollow delivery tip; and a hollow, flexible adaptor which flexibly couples the delivery tip in fluid communication with the two-part material delivery system such that the two-part material delivery system can be remotely held relative to the hollow delivery tip, wherein the adaptor has a septum therein, the septum dividing the adaptor into first and second separate lumens extending along the length of the adaptor, such that first and second materials delivered from the two-part material delivery system are retained in the separate lumens until reaching the hollow delivery tip, thereby preventing the first and second materials from mixing with each other until reaching the deliver tip.

18. A dispensing system as recited in claim 17, wherein the adaptor comprises a flexible, elongate tube, and wherein the delivery tip comprises a substantially rigid hollow tip selectively, removably coupled in fluid communication with the tube.

19. A dispensing system as recited in claim 17, further comprising a cover for selectively, removably covering the flexible adaptor.

* * * * *

UNITED STATES PATENT AND TRADEMARK OFFICE
CERTIFICATE OF CORRECTION

PATENT NO.    : 6,234,795 B1
DATED         : May 22, 2001
INVENTOR(S)   : Dan E. Fischer It is certified that error appears in the above-identified patent and that said Letters Patent is hereby corrected as shown below:

Column 1,
Line 53, after "patient" delete [.]

Column 3,
Line 52, change "delivery" to -- deliver --

Column 12,
Line 18, change "two-pat" to -- two-part --
Line 20, change "deliver" to -- delivery --

Signed and Sealed this

Sixteenth Day of April, 2002

Attest:

JAMES E. ROGAN
Attesting Officer        Director of the United States Patent and Trademark Office